United States Patent
Weston

[11] Patent Number: 5,957,886
[45] Date of Patent: Sep. 28, 1999

[54] SPRING-POWERED DISPENSING DEVICE

[75] Inventor: Terence Edward Weston, Suffolk, United Kingdom

[73] Assignee: Weston Medical Limited, Suffolk, United Kingdom

[21] Appl. No.: 08/913,254

[22] PCT Filed: Mar. 8, 1996

[86] PCT No.: PCT/GB96/00551

§ 371 Date: Sep. 10, 1997

§ 102(e) Date: Sep. 10, 1997

[87] PCT Pub. No.: WO96/28202

PCT Pub. Date: Sep. 19, 1996

[30] Foreign Application Priority Data

Mar. 10, 1995 [GB] United Kingdom ............... 9504878

[51] Int. Cl.⁶ .......................... A61M 5/30; A61M 5/315
[52] U.S. Cl. ............................... 604/68; 604/230
[58] Field of Search .................... 604/181, 187, 604/208, 218, 220–222, 225, 228, 230, 236, 131, 134–137, 143, 147, 68; 73/430; 267/137; 175/321; 123/451

[56] References Cited

U.S. PATENT DOCUMENTS

| | | |
|---|---|---|
| 3,797,489 | 3/1974 | Sarnoff. |
| 4,194,582 | 3/1980 | Ostertag .................... 175/321 |
| 4,237,881 | 12/1980 | Beigler et al. ............. 604/118 |
| 4,611,742 | 9/1986 | Werner et al. . |
| 4,744,786 | 5/1988 | Hooven ..................... 604/143 |
| 5,069,317 | 12/1991 | Kurt et al. . |
| 5,083,623 | 1/1992 | Barrington .................. 175/321 |

FOREIGN PATENT DOCUMENTS

| | | |
|---|---|---|
| 0276158 | 7/1988 | European Pat. Off. . |
| 0409674 | 1/1991 | European Pat. Off. . |
| 0510826 | 10/1992 | European Pat. Off. . |
| 0653220 | 5/1995 | European Pat. Off. . |
| 95/03844 | 2/1995 | WIPO . |

*Primary Examiner*—Corrine McDermott
*Assistant Examiner*—Sharon Finkel
*Attorney, Agent, or Firm*—McDermott, Will & Emery

[57] ABSTRACT

A needleless injector is described for dispensing a liquid material, comprising a dispensing member which moves under the force of a spring providing an energy store. A damping arrangement, employing a viscous damping medium such as grease, is used to damp recoil during dispensing.

9 Claims, 3 Drawing Sheets

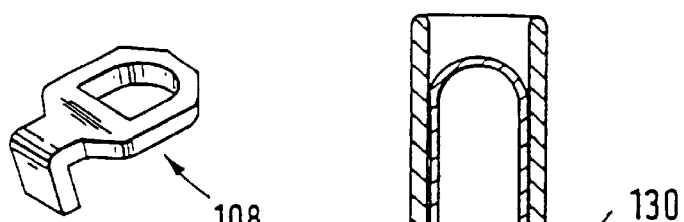
FIG.3a.
FIG.3.
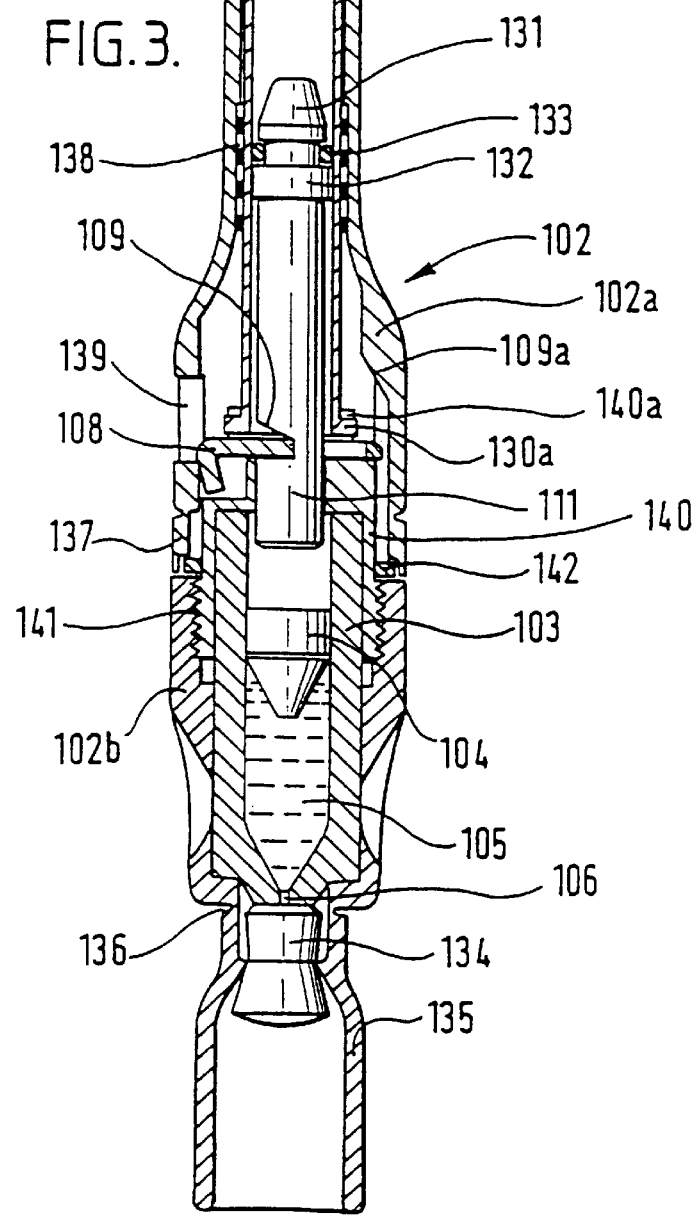

SPRING-POWERED DISPENSING DEVICE

FIELD OF THE INVENTION

This invention relates to a dispensing device which employs a spring (which may, for example, be of metal or compressed gas) to urge a dispensing member to dispense, for example, a dose of liquid, powder, or a pellet.

BACKGROUND OF THE INVENTION

Spring powered dispensers are in common use. For example in the medical field, there are automatically operated injectors for delivering medicaments to the tissues. Generally the device is placed on the patient's skin, and a release button is operated which unlatches a pre-loaded spring that drives the hypodermic needle through the epidermis, and thereafter pumps the medicament into the tissues. At the instant of release, the housing of the injector reacts against the mass of the driven piston in the reverse direction of the injection—that is, it recoils. This is wasted energy, although in the case of simple injectors, the recoil is resisted by the user's hand, and a larger proportion of the spring force is directed to moving the needle and medicament.

More sophisticated devices aim to apply a predetermined force to the skin, so that the optimum placement conditions are met before the device may be operated. Examples of the latter may be found in the needleless injectors disclosed in PCT/GB94/01608 (WO95/03844) by the present inventor. In these examples it is convenient to apply the force via a sleeve or ring acting through a spring, so that the user grasps the sleeve or ring, and presses the delivery orifice of the injector onto the skin. When the displacement of the sleeve reaches a predetermined value corresponding to the desired contact force on the skin, it operates a release mechanism which causes the injection. At the instant of release, the injector body, which is effectively "floating" within the operating sleeve, recoils away from the injection site, reacting against the operating sleeve spring. This represents wasted energy, since ideally, all of the spring energy should be directed to driving the medicament into the tissues, not in moving the injector body in the opposite direction.

It is possible to use a substantial spring to urge the injector via the operating sleeve onto the patient's skin, and thereby reduce the recoil by coupling the injector body through the spring and sleeve to the mass of the user's hand. However, this results in an unacceptably high pressure on the skin and/or trigger mechanism. For example, a needleless injector must be pressed onto the skin with a relatively light force for a subcutaneous injection, otherwise the subcutaneous tissues are compressed too much, resulting in a faulty injection.

Other devices which may employ pre-loaded spring energy to deliver a metered dose of liquid or powder, include breath-actuated metered dose inhalers (MDI's), automatic bactericide dispensers, and guns. In all cases where the user does not hold the device member on which the power spring reacts there is the potential of energy wastage. Many of these devices are intended for single use, or must be discrete—that is, small and lightweight, and it is important that the stored energy is used efficiently.

SUMMARY OF THE INVENTION

According to the present invention there is provided a device for dispensing a material or article comprising a dispensing member movable, to effect dispensing, under the force of a spring which provides an energy store, and damping means, having a viscous damping medium, for damping recoil of the device during dispensing.

In a preferred embodiment, the invention is applied to a needleless injector. We have obtained significant improvements in operating characteristics of a needleless injector by applying the skin contact force to the injector body via an operating sleeve coupled to the injector body by a highly viscous grease. The grease is sufficiently soft to permit relatively slow sleeve displacement to operate the release mechanism, but at the instant of release the high viscosity grease prevents the rapid recoil of the injector body relative to the operating sleeve. Of course, the injector is coupled momentarily to the operating sleeve, so that the combination attempts to recoil, but since at the instant of release the user's hand is firmly gripping the sleeve, most of the recoil is prevented, and a higher proportion of the power spring energy is employed in dispensing the injectate.

A further benefit arising from the invention that the risk of inadvertent operation is greatly reduced, since trigger operating resulting from a sharply applied force (caused by dropping the injector, clumsy handling, or too rapid application) is resisted by the damping grease.

In a preferred embodiment, a needleless injector having a cylindrical body is operated by pressing the discharge nozzle onto the patient's skin by acting on a close-fitting concentric sleeve, which, when displaced relative to the injector body releases the spring powered ram to cause the injection. A longitudinal groove in the wall of the injector body contains the high viscosity grease, and a cooperating key on the operating sleeve is a close sliding fit in the groove. Gentle pressure on the sleeve causes it to move on the injector body in a smooth, damped motion; rapid movement is strongly resisted by the high viscosity grease which inhibits the key from paid movement in the groove. When the injector "fires", the injector body tries to react very rapidly. However, it can move only a very small distance relative to the operating sleeve because of the grease, and is thereby coupled to the operating sleeve through the said grease. The mass of the sleeve resists motion, and since the sleeve is being held firmly by the user, the mass of the user's hand is added to that of the sleeve, thus further reducing recoil motion.

BRIEF DESCRIPTION OF THE DRAWINGS

In the accompanying drawings:

FIG. 3 is a section on the longitudinal axis of a second embodiment of needleless injector, and showing the injector prior to use; and FIG. 3a shows on a larger scale a latch used in FIG. 3.

DETAILED DESCRIPTION OF THE INVENTION

Figure 1:
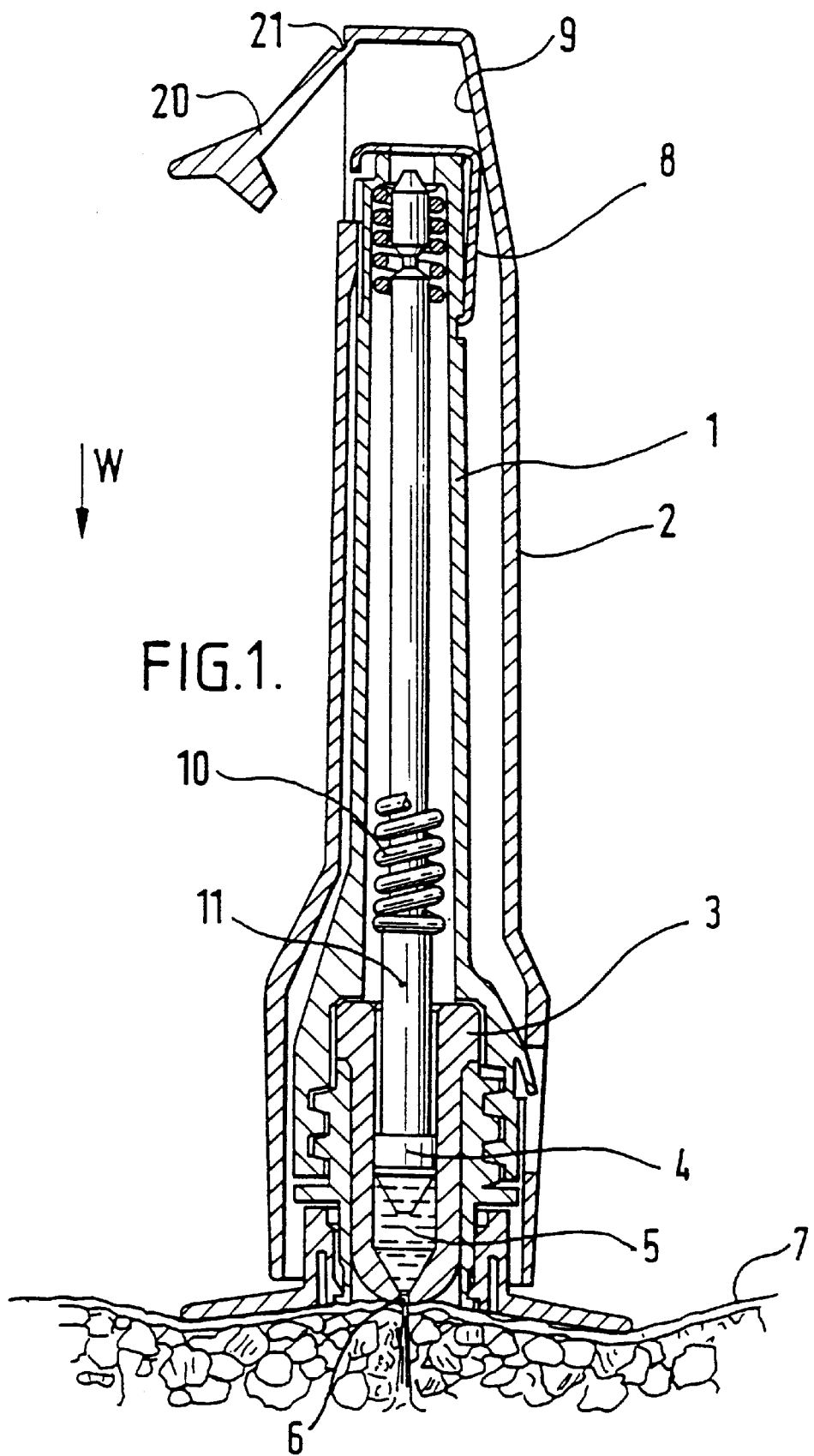
FIG. 1 shows a section on the longitudinal axis of a first embodiment of a needleless injector according to the invention, with the components positioned to show the device in mid-injection.

Referring to FIG. 1, which shows the first embodiment of injector in mid-injection, the injector comprises an inner body 1 which is closely located within, but free to slide longitudinally with respect to, an operating sleeve 2. The sleeve 2 has a safety catch 20 integral therewith and pivotal with respect to the remainder of the sleeve by a living hinge 21. The latch is shown in the open position in FIGS. 1 and 2. The injector contains a medicament cartridge 3 which is firmly attached to the body 1, and which has a piston 4 slidingly and sealing located therein, in contact with medicament 5. As considered from the upper end of FIG. 1, the piston comprises a cylindrical portion, a larger diameter cylindrical sealing portion, and a frusto-conical portion. The cartridge 3 has a discharge orifice 6.

Figure 2:
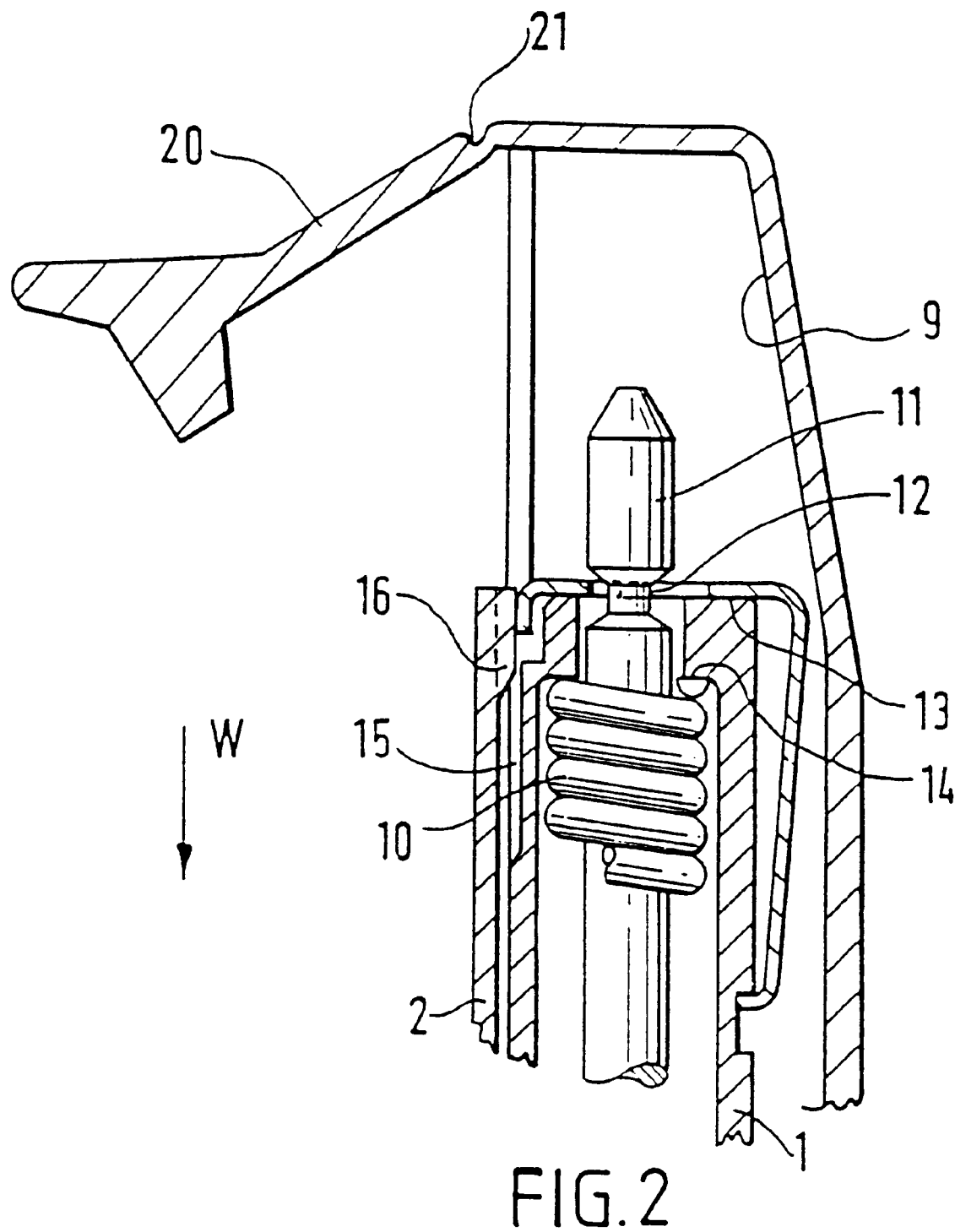
FIG. 2 is an enlarged portion of the injector shown in FIG. 1, showing the cooperating groove and key, and the trigger mechanism prior to operation.

Referring to FIG. 2, which is an enlarged view of the injector trigger mechanism just prior to operation, injector body 1 houses a helical compression spring 10 which urges a ram 11 in direction of arrow W, but ram 11 is prevented from movement by a latch 8 engaging with a groove 12 on ram 11. The thrust of the ram 11 on latch 8 is taken on a face 13 of body 1, and the reaction of spring 10 is taken on a face 14 of body 1. Body 1 has a groove 15, and operating sleeve 2 has a key 16 which is a close sliding fit within the said groove. Groove 15 contains a viscous grease, which damps relative movement of the key 16 in groove 15: ipso facto, relative movement between sleeve 2 and body 1 will be damped.

Referring to both FIGS. 1 and 2, which show the safety catch already in the open position of the injector is operated by grasping the operating sleeve 2 in the hand, and, placing orifice 6 onto the patient's skin 7, pressing in direction of arrow W. This causes the sleeve 2 to move relative to the body 1, causing a cam surface 9 to release latch 8 from groove 12 of ram 11. Spring 10 accelerates ram 11 rapidly in the direction of arrow W, so that it strikes piston 4 in cartridge 3 to dispense the injectate in known manner.

At the instant of release, the spring 10 urges ram 11 in the direction of arrow W, as described, but the spring also reacts on body 1 at face 14, so that the body 1 tries to move in the opposite direction to arrow W. There will be two reaction phases; the first at the instant of release, when the reaction force is on body 1 is against the mass of ram 11, and the second when the reaction force is against the combined mass of the cartridge 3 and body 1. However, this second reaction in within the closed combination of the firmly attached cartridge 3 and body 1, and there are few losses. However, the first reaction represents wasted energy, and furthermore tends to cause the body and cartridge combination to jump away from the injection site, thereby breaking the hydraulic connection to the skin and resulting in leakage of medicament. This first reaction is substantially reduced by the damping grease in groove 15.

Many variations in the described embodiment are possible. For example the damping grease may be retained within a circumferential groove on body 1 which is a close sliding fit within the operating sleeve 2 (see, for example, the embodiment of FIG. 3). In all cases it is simple to vary the viscosity or running clearance to obtain the desired damping characteristics. Further modification to the damping characteristics are possible by using dilatant or shear-thickening compounds.

The use of a damping grease through which to apply the trigger release conditions results in rate sensitivity—that is, if the operator applies a very high operating thrust to trigger the injector, at least some of this excessive force will be applied to the skin at the instant of injection. However, in practice, the range of forces applied by users is within sensible limits, and very consistent results are obtained.

The embodiment of FIG. 3 is similar to that of FIGS. 1 and 2 in various respects, and elements in FIG. 3 which correspond substantially to particular elements in FIGS. 1 and 2 are given the same reference numerals but increased by 100.

In the embodiment of FIG. 3, the mechanical spring used in the embodiment of FIGS. 1 and 2 is replaced by a compressed gas spring. This is provided by a cylinder 130 which is closed at its upper end and which contains gas, typically air, under a pressure which is typically in the range 5.5 MPa (800 psi) to 20.7 MPa (3000 psi). The upper end of the ram 111 has a frustoconical portion 131 and a flange 132 between which is situated an O-ring seal 133. Prior to use, the ram 111 is held in the illustrated position by latch 108 engaging in a groove in the ram, the upper surface of the groove forming a cam surface 109. The latch 108 is shown on a larger scale in FIG. 3a. At this point the latch is unable to move leftwards, because it bears against the inner wall of the sleeve 102.

The lower end of the cylinder 130 has an outwardly directed flange 130a, which enables the cylinder to be held by crimping the flange 130a beneath an outwardly directed flange 104a at the upper end of coupling 140. The sleeve 102 is formed of an upper portion 102a within which the cylinder is situated, and a lower sleeve portion 102b. The sleeve portion 102b is connected to the coupling by the interengaging screw threads 141 formed on the inner and outer walls of the sleeve portion 102b and coupling 140 respectively.

The orifice 106 is sealed by a resilient seal 134 which is held in place by a seal carrier 135. The seal carrier 135 is connected to the lower sleeve portion 102b by a frangible joint 136.

As a precaution against accidental firing, a tear-off band 137 is provided as the lower part of the upper sleeve portion 102a. The lower edge of the tear-off band 137 bears against a ring 142 which is bonded to the exterior surface of the coupling 140 or (not shown) formed integrally therewith. The function of the ring is to prevent downward movement of the sleeve portion 102a relative to the coupling 140, for so long as the tear-off band 137 is present. Accordingly, the ring 142 need not extend completely around the periphery of the coupling, and could be replaced by one or more separate elements.

An annular space 138 is formed in the inside wall of the sleeve 102. Where the sleeve is adjacent the cylinder 130, and the space is filled with a damping grease (indicated diagrammatically by a succession of black bands), so that the grease is in intimate contact both with the sleeve 102 and the cylinder 130. It should be noted that although a defined annular space is convenient from the point of view of providing a particular location for the grease, it could be omitted and the grease simply smeared over all or part of the outside of cylinder 130 and/or inside of sleeve 102.

When the embodiment of FIG. 3 is to be operated, the user snaps off the seal carrier 135 at the frangible joint 136, which takes the seal 134 with it and exposes the orifice 106. The user then removes the tear-off band 137, and grasping the upper part of the sleeve 102 urges the orifice against the substrate (e.g. the user's own skin) which is to be injected. This moves the upper sleeve portion 102a downwardly, with respect to the lower sleeve portion 102b. This brings the aperture 139 into alignment with the latch 108, which is thus able to move sideways into the aperture under the influence of the force of gas within the cylinder 130 acting on the latch via the cam surface 109 formed in the ram 111. The injector is thus caused to fire. As a precaution, in case the latch fails to move under the influence of the cam surface 109, an auxiliary cam surface 109a is provided on the inside of the sleeve portion 102a. As with the embodiment of FIGS. 1 and 2, the resulting recoil is damped by the damping grease.

By way of example only, the following are typical measurements for the embodiment of FIG. 3:

| | |
|---|---|
| Diametrical clearance between gas cylinder outside diameter and sliding sleeve inside diameter | 0.05 mm |
| Area of shear (i.e. cross section of grease) approximately | 375 mm$^2$ |
| Viscosity of grease | 2.2 Kilopoise |
| Momentum of ram at impact | 0.06 kg × m/s |
| Mass of sleeve portion 102a | 1.3 g |
| Mass of ram | 2.5 g |
| Impact gap between ram and piston | 4 mm |
| Gas pressure | 6.2 MPa |
| Bore of gas cylinder | 5.0 mm |

Whilst grease has been discussed as a preferred damping medium, similar results may be obtained by using air or oil damping devices—usually a cylinder and piston combination, i.e. a so-called "dashpot", wherein a fluid substance is caused to flow through a restriction, thereby to resist motion. Other viscous damping devices employ a vane, or a plurality of vanes, spinning in a damping medium, for example air, and these may be used if appropriate to the particular application.

I claim:

1. A needleless injector comprising:

a first, user-holdable member, a second member which is movable with respect to the first member, the second member having a liquid outlet for a liquid to be injected into a subject, and a dispensing member movable to expel the liquid through the outlet under the force of a spring which provides an energy store, , and damping means, comprising a viscous damping medium, operable to damp movement of said first member with respect to said second member.

2. A needleless injector according to claim 1, further comprising:

a cartridge, which contains the liquid, and a free piston disposed in the cartridge in contact with the liquid, a latch, and wherein:

the dispensing member comprises an impact member urged by the spring and temporarily restrained by a latch, the impact member being movable in a first direction under the force of the spring to first strike the free piston and then to continue to move the piston in the first direction to expel a dose of liquid through the liquid outlet.

3. A needleless injector according to claim 2, wherein the latch is arranged to be released by movement of the first member with respect to the second member in the first direction.

4. A needleless injector according to claim 1, wherein said damping means further comprises:

a groove formed in one of said first and second members and having a viscous damping medium therein, and an element which is formed on the other of the first and second members and which is arranged, in use, to travel through said viscous damping medium to effect damping.

5. A needleless injector according to claim 1, wherein the viscous damping medium is a grease.

6. A needleless injector according to claim 1, wherein the viscous damping medium is an oil.

7. A needleless injector according to claim 1, wherein the viscous damping medium is air.

8. A needleless injector according to claim 1, wherein said spring is a mechanical spring.

9. A needleless injector according to claim 1, wherein said spring is a compressed gas spring.

\* \* \* \* \*